United States Patent [19]

Correa et al.

[11] 4,394,573
[45] Jul. 19, 1983

[54] METHOD AND APPARATUS FOR UNDERWATER DETECTION OF HYDROCARBONS

[75] Inventors: Aderbal C. Correa; John S. Gergely, both of Ponca City, Okla.; Andrew J. Blanchard, College Station, Tex.

[73] Assignee: Conoco Inc., Ponca City, Okla.

[21] Appl. No.: 216,137

[22] Filed: Dec. 15, 1980

[51] Int. Cl.$^3$ .................... G01V 5/00; G01T 1/167
[52] U.S. Cl. .................................. 250/253; 250/301; 250/573
[58] Field of Search .............. 250/253, 301, 365, 372, 250/373, 458, 459, 461 R, 461 B, 224, 573; 356/317, 318, 417, 70

[56] References Cited

U.S. PATENT DOCUMENTS

| | | | |
|---|---|---|---|
| 3,546,456 | 12/1970 | Grice | 250/360 |
| 3,736,428 | 5/1973 | Monroe | 250/253 |
| 3,899,213 | 8/1975 | Fantasia et al. | 250/301 |
| 3,961,187 | 6/1976 | Barringer | 250/253 |
| 4,178,512 | 12/1979 | Früngel et al. | 250/253 |
| 4,293,225 | 10/1981 | Wheaton et al. | 250/461 R |

OTHER PUBLICATIONS

Sheives, T. C., "A Study of Dual Polarization Laser Backscatter System for Remote Identification and Measurement of Water Pollution", Texas A & M University Technical Report, No. RSC-53, 1974.

Primary Examiner—Janice A. Howell
Attorney, Agent, or Firm—William J. Miller

[57] ABSTRACT

Method and apparatus for detecting the presence of hydrocarbons and other substance that fluoresces or absorbs light within a body of water which utilizes a controlled submersible vehicle scanning at or near the water bottom. The method utilizes a selected frequency light source as carried by the submersible to scan the water bottom, and the returned light energy, either at the wavelength of oil fluorescing in water or the source frequency backscatter, is detected and processed for the water bottom as well as a water region that is a selected distance above the water floor. Alternative forms of apparatus are disclosed for carrying out the functions of both oil fluorescence detection, and for obtaining differential absorption readings as to light source backscatter energy that is created by the ambient water and other factors in the water environmentsuch as marine life, turbidity, etc.

23 Claims, 8 Drawing Figures

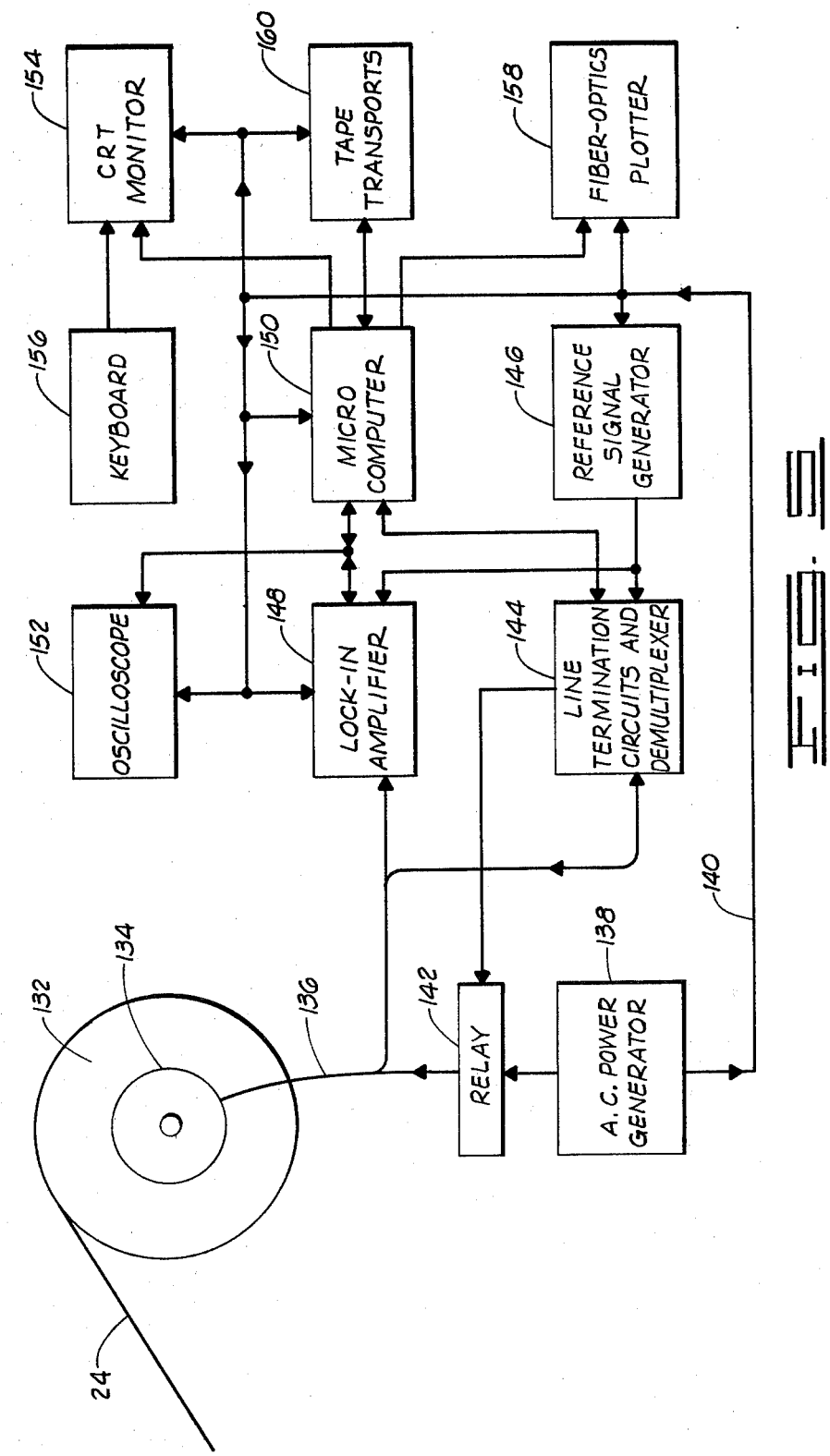

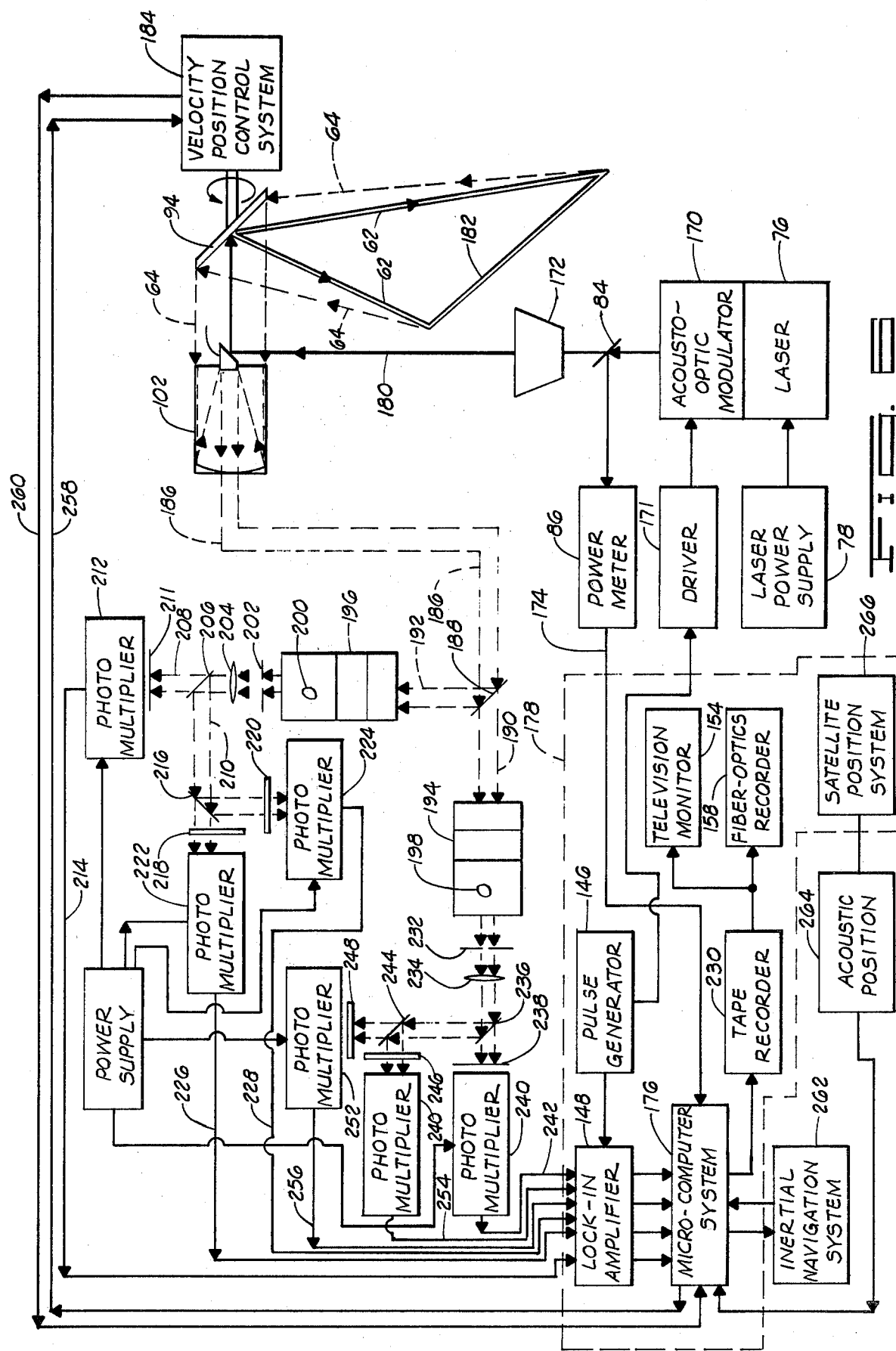

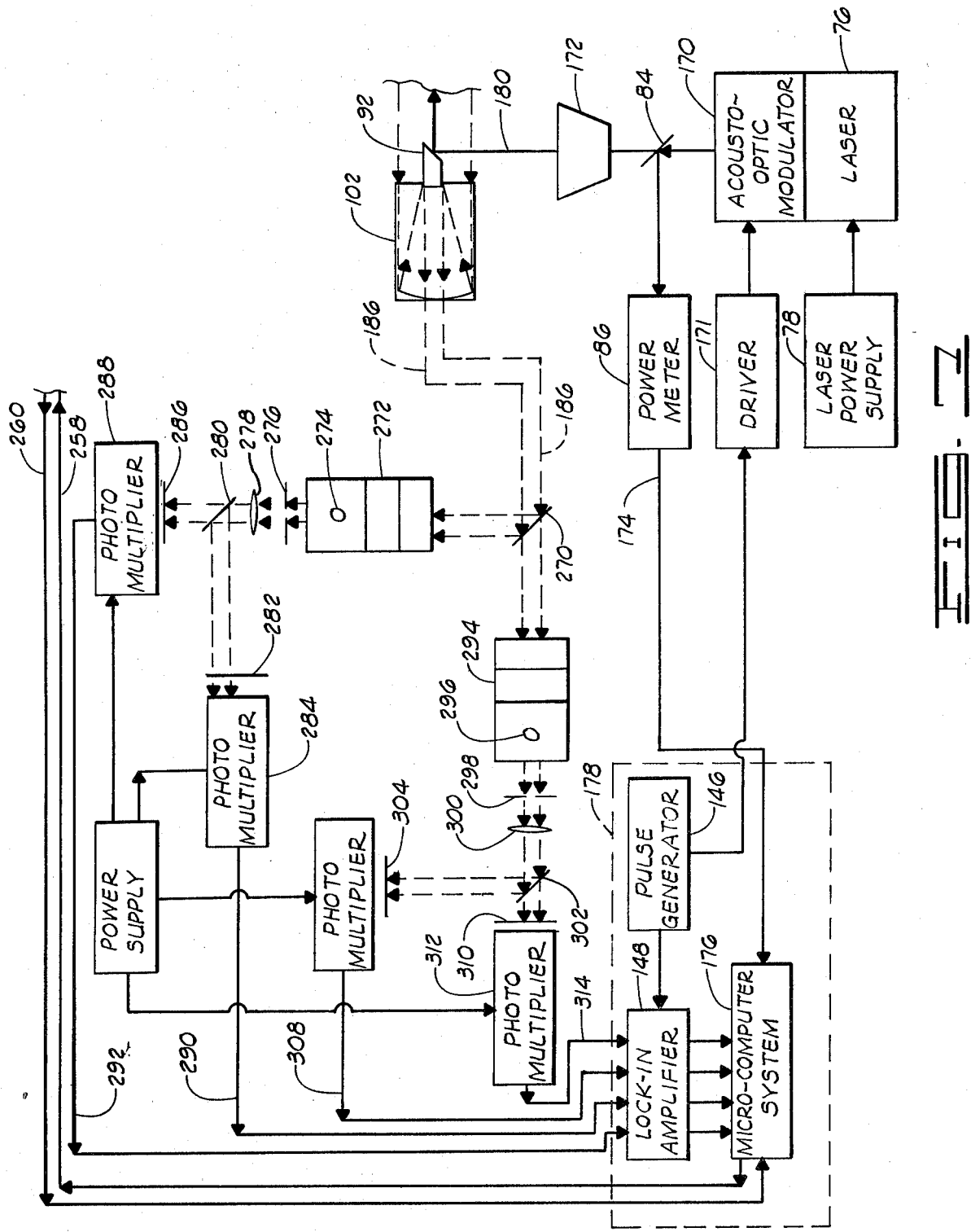

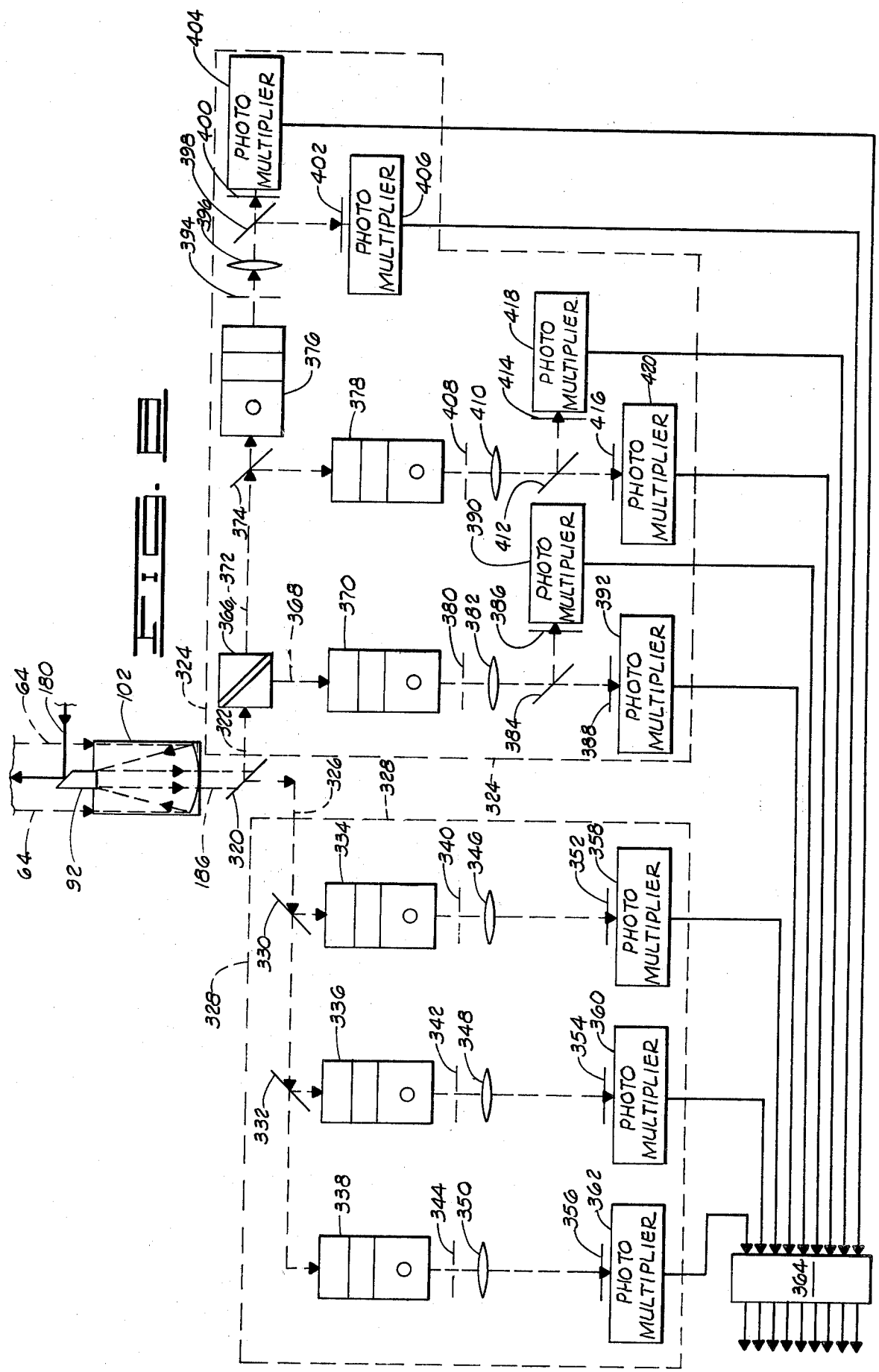

METHOD AND APPARATUS FOR UNDERWATER DETECTION OF HYDROCARBONS

BACKGROUND OF THE INVENTION

1. Field of the Invention

The invention relates generally to method and apparatus for deriving hydrocarbon indications underwater and, more particularly, but not by way of limitation, it relates to improved detection methods for locating oil presence and seep sources on the sea floor and within a body of water.

2. Description of the Prior Art

The prior art includes numerous systems that are utilized for actively detecting the presence of hydrocarbons such as result from oil spills and the like on the surface of both earth and water. Such prior art systems have utilized microwave radiation, ultra violet illumination, laser beams and the like to initiate key responses which are then scanned from remote positions, such as an airborne platform. Some representative U.S. Patents falling in this category are U.S. Pat. Nos. 3,899,213, Fantasia, et al.; 3,961,187, Barringer; and, 3,736,428, Monroe. These prior active systems all function to detect reflectance, luminescence, or emittance characteristics of oil on the water surface and such systems necessarily operate from a remote platform such as an airborne vehicle or water vessel.

Direct detection of oil or other hydrocarbon products below the sea surface has been carried out heretofore by means of geochemical prospecting techniques. One technique involves the detection of hydrocarbon seepage through the analysis of hydrocarbons dissolved in sea water. Another technique relies on the analysis of bottom sediment samples for their hydrocarbon content. The sea water sampling method requires very sensitive analytical techniques because the hydrocarbon gases dissolved in sea water are rapidly dispersed by marine currents. Bottom sediment analysis applies the same principles that govern soil sediment prospecting on land surface. The sampling is generally at least two or four meters beneath the sea bottom in order to avoid contamination by organic matter at or near the bottom, and accumulated samples are then treated with acids while liberated hydrocarbon gases are analyzed by gas chromatograph or the like. None of the prior methods readily provide an accurate indication of the position of the source of seepage on the ocean floor. Moreover, hydrocarbon gas concentrations in water or bottom sediments may originate from sources other than subsurface hydrocarbon deposits or pipelines, such as decomposition of organic matter.

SUMMARY OF THE INVENTION

The present invention relates to an underwater detection method and active optical system for detection of the presence of oil dispersed in water as well as at the bottom-sediment water interface, i.e. as opposed to detection of discrete oil slicks accumulating on the water surface. The basic system is composed of an excitation source, fluorescence and/or laser backscatter receiving equipment, submersible platform and stabilization equipment and data acquisition electronics. The excitation source within a submersible consists of a laser transmitter operating at specified wavelengths that are optimum relative to transmissivity and scattering in a marine environment while also affording optimum fluorescence excitation wavelengths. A scanning optical system then provides selected directivity to the laser beam along the water bottom with reflection of fluorescent light to the receiver equipment for conversion and electrical signal processing indicating presence and degree of hydrocarbon-related fluorescent activity and backscattering. Additional equipment within the underwater submersible provides equipment power supplies, timing control and data ordering for transmission from the submersible back to the mother vessel and the computational, storage and monitoring equipment.

Therefore, it is an object of the invention to provide a method and apparatus for detection of hydrocarbons or other fluorescing substance underwater and on the sea floor.

It is yet another object of this invention to provide capability of accurate discrimination between water body fluorescence due to hydrocarbons and that caused by organic life and decomposed matter.

It is still further an object of the present invention to provide a water bottom scanning lidar system which provides selective three-dimensional indication proximate the water bottom or other selected locale.

Finally, it is an object of the invention to provide a system which generates true indication of hydrocarbon-presence fluorescence to the exclusion of interfering responses from such as turbidity and other sources of backscattered energy.

Other objects and advantages of the invention will be evident from the following detailed description when read in conjunction with the accompanying drawings which illustrate the invention.

BRIEF DESCRIPTION OF THE DRAWINGS

FIG. 5 is a block diagram of shipboard equipment utilized in conjunction with the submersible equipment;

FIG. 6 is a detailed block diagram of the circuitry and optics utilized in a laser scanning system of the present invention;

FIG. 7 is a block diagram of a scanning system for detecting differentially absorbed scattered energy, an alternative method for detecting the presence of oil which is independent of the effects of turbidity; and FIG. 8 is a block diagram of an alternative form of scanning system which combines fluorescence detection and determination of absorbed scattered energy.

DETAILED DESCRIPTION OF THE INVENTION

In the present invention, a laser beam is utilized to induce petroleum fluorescence for the purpose of detecting and measuring oil and related hydrocarbon products within a water body. The device will not only detect oil dispersed in a water column, but will scan the bottom of the water body and pinpoint the actual area of seepage. The latter feature is particularly desirable in view of the fact that oil detected in a water column may have drifted miles from the actual point of seepage. Thus the present system may be used in pollution monitoring, both natural and around offshore drilling and production facilities, and in detecting leakage in underwater pipelines and detecting natural seeps which may be related to exploration targets.

Figure 1:
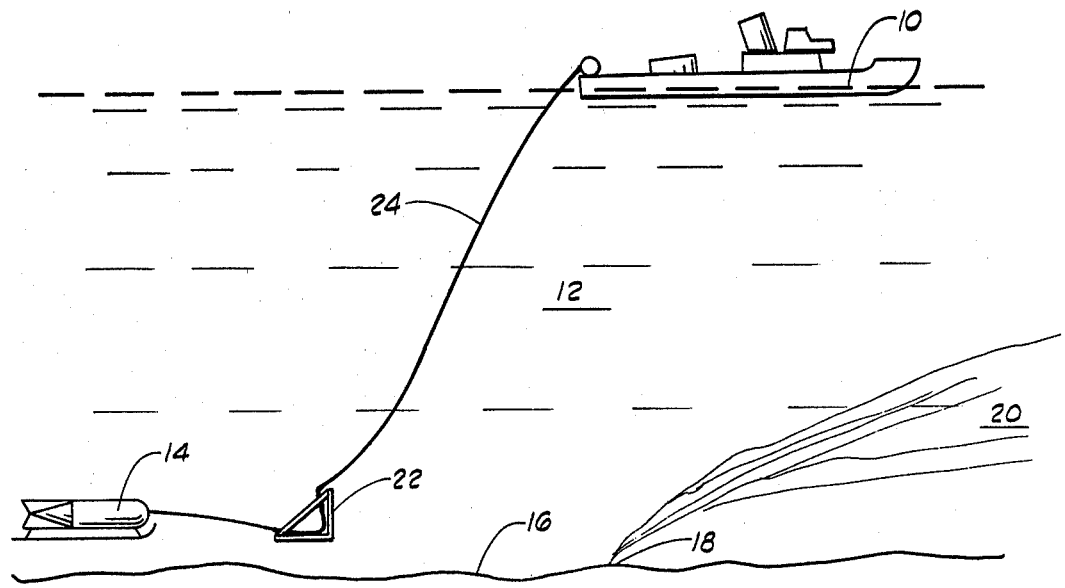
FIG. 1 is a schematic illustration of a towed submersible in operational attitude.

FIG. 1 illustrates the general mode of operation wherein a survey vessel 10 on a body of water 12 is employed to tow a submersible sensor 14 at a designated depth above water bottom 16. Hydrocarbon pollution is shown as a seep fissure or source 18 giving rise to a plume 20 of hydrocarbon as it drifts with the current. In the FIG. 1 case, the submersible sensor 14 is a towed vehicle controlled by a depressor platform 22 and tow cable 24 from the stern of tow vessel 10. The operation depth of such a system utilizing the towed sensor may be as deep as 6000 meters to water bottom.

Figure 2:
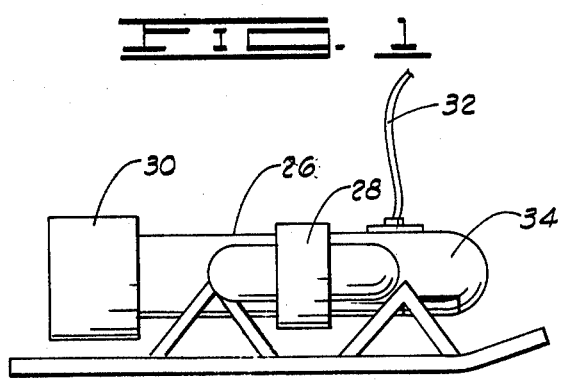
FIG. 2 is a side elevation of an alternative, remotely controlled form of submersible.

FIG. 2 illustrates an alternative form of submersible 26 which may be utilized to carry the sensor equipment. Such manned or unmanned submersibles, also known as remote controlled vehicles (RCV), are commercially available and include vertical thrusters 28 and main thruster 30 as controlled by communication through umbilical cable 32 extending upward from sensor housing 34 to the mother vessel 10. The operation of an unmanned submersible vehicle 26 is remotely controlled from the surface vessel which also provides to the craft the electrical power necessary for propulsion and remote sensing operations. The umbilical line 32 carries control commands to the submersible 26 and transmits data back to the surface. Since power is supplied from the surface, this vehicle can stay submerged for indefinite periods and has the capability of carrying out activities at great depths.

The sensor vehicle 14 (or 26) utilizes the fluorescent excitation source consisting of a laser transmitter operating at a specified wavelength or several wavelengths simultaneously. Wavelength selection is a particularly critical factor since several other operating conditions are influenced. Some of these include optical transmissivity and scattering in the marine environment, fluorescence excitation, background (i.e., unwanted) fluorescence phenomena and physical selection criteria for laser transmitters such as power, size, ruggedness, etc.

Selection of laser source will depend primarily upon radiation wavelength, power output capability and reliability. Incident radiation at approximately 430–460 nanometers wavelength will stimulate fluorescence from oil which peaks in the 490–510 nanometer wavelength range, and fluorescence from marine phytoplankton which peaks at about 660 nanometers. Further, it is known that chemically-induced bioluminescence from Marine Euphausiid and Marine Dinoflagellate organisms peaks sharply at 465 nanometers. This peak separation allows discrimination as between oil fluorescence and fluorescence induced in some common marine organisms. Thus, while the most promising wavelength in oil exists in the ultraviolet spectrum, still other excitation wavelengths exist in the blue wavelength region.

Figure 3:
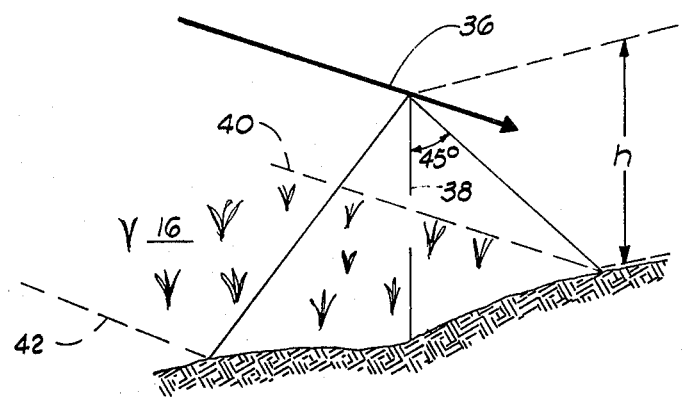
FIG. 3 is a schematic illustration of sensor forward movement and scanning registration along the sea floor.

FIG. 3 illustrates schematically the mode of operation of the submerged sensor vehicle as it is propelled along a survey line 36 generally parallel to the water bottom 16 at a designated height h thereabove. The laser scanning mechanism aboard the sensor vehicle is then controlled to repetitively scan across the progression path through an angular excursion of typically 45° to either side of a vertical line 38. Scanning speed may be adjusted relative to submersible 14 movement thereby to provide adjustment of the scanning resolution along the water bottom swath lying between dash lines 40 and 42. The scanning path or survey line 36 may be adjusted in accordance with the exigencies of a particular operation since various factors such as turbidity, decaying marine life and the like will affect light transmissivity near bottom 16; however, it is contemplated that under optimum conditions the sensor vehicle 14 will be able to move from 50 to 100 feet above water bottom 16.

Figure 4:
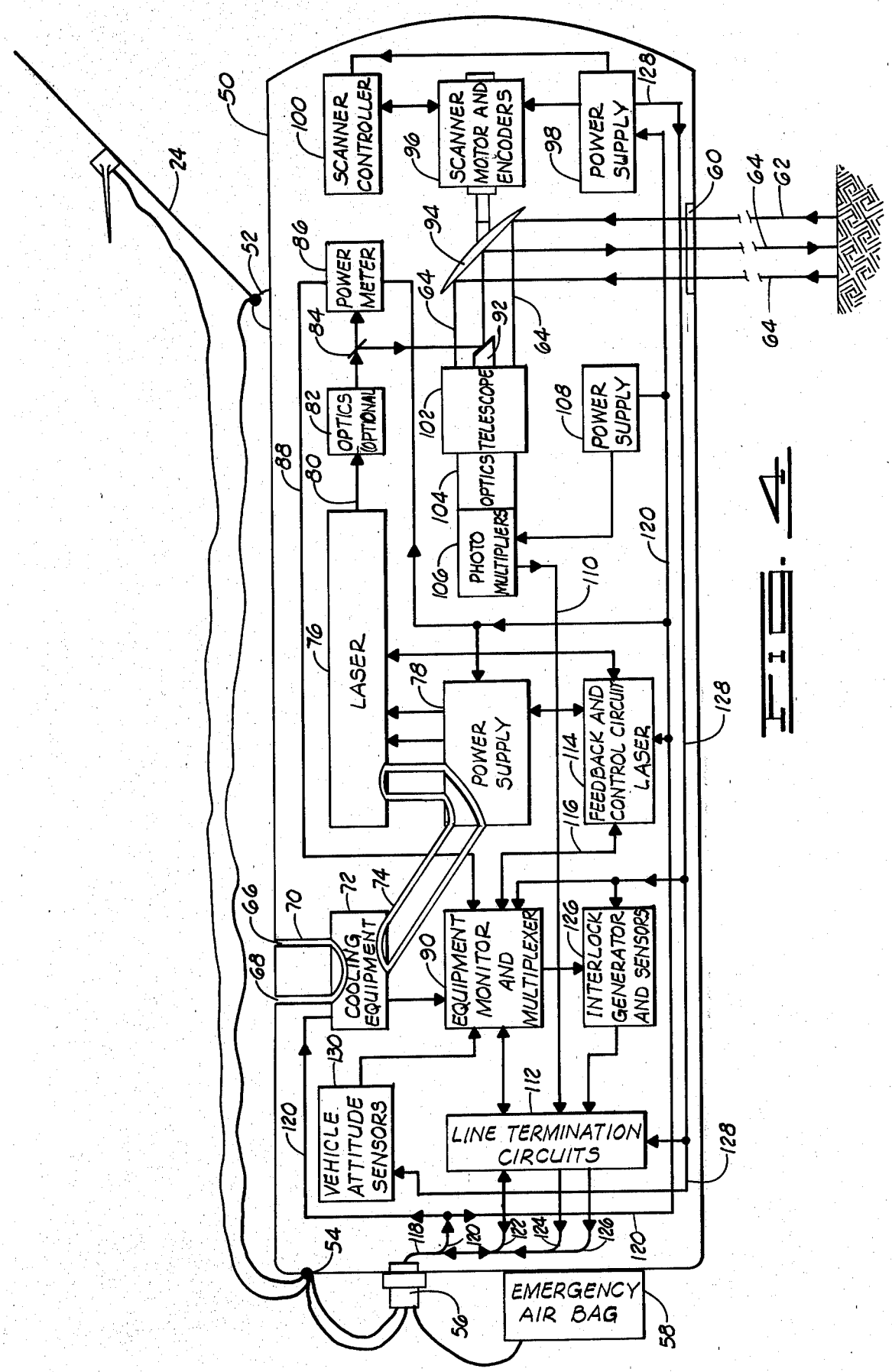
FIG. 4 is a block diagram illustrating a general form of submersible equipment for providing underwater active surveillance for hydrocarbons.

FIG. 4 illustrates a submersible instrument housing 50 in general block form. The housing 50 is an integral part of either the towed vehicle 14 or the unmanned submersible vehicle 26, but it is illustrated in conjunction with a tow cable 24. Tow cable 24 is a conventional form of cable which includes the necessary stress-resistant cable and telemetric communication lines for interconnection between tow vessel 10 and the submersible. Tow cable 24 is attached to a first tow point 52, a breakaway tow point, and extends from there aft to a permanent recovery tow point 54 as the electrical conduit connections are extended through a water-tight feed-through connector 56 to the interior of housing 50. A recovery air bag 58 may be included for actuation either remotely or from selected alarm circuitry on-board housing 50.

The front portion of housing 50 includes an arcuate window 60, formed of suitable ray transmissive material which extends around the forward under side of housing 50 sufficiently to provide the requisite transverse scan acquisition. Both the outgoing light beam 62 and the responding fluorescent light rays 64 pass through the window 60, as will be further described. External water is utilized for cooling necessary components within housing 50 as a water inlet 66 and outlet 68 communicate via conduit 70 with the on-board cooling equipment 72. Cooling equipment 72, of conventional type, then provides coolant circulation by means of conduit 74 to the laser 76 and high-voltage power supply 78.

Numerous types of laser 76 may be utilized for providing the scanning light output. At present, both Argon and Helium Cadmium are utilized and the former is preferred due to its higher power output capabilities and reliability. Also, those wavelengths emitted by the Argon laser place interfering signals (RAMAN) outside the pass band for oil fluorescence. Thus, laser 76 may be an Argon laser emitting in the blue range around 454–514 nanometers as is commercially available from Lexel Corporation, Palo Alto, California. Optionally, the laser output beam 80 may be beam expanded by optics 82 for the purpose of instantaneously illuminating a larger volume of water so a survey area can be convered more completely. The output beam 80 then experiences a 90° reflection from a 92% beam splitter 84, the lesser beam output being intercepted by a power meter 86 which provides a control output via line 88 to the system monitor and multiplexer 90. The remaining portion of output beam 80 from beam splitter 84 is again 90 degree reflected from prism 92 to a rotating elliptical or pyramidal scanning mirror 94 whereupon it is directed through the window 60 as the output scanning beam 62 continually traverses the path beneath housing 50.

It should be understood that the system will also function using a pulsed laser source. Still alternatively, the source may be a dye laser, arc lamp or any radiation source of specified wavelength capable of emitting a collimated light beam.

The scanning mirror 94 is controlled by conventional scanner motor and encoders 96 as energized by power supply 98 and controlled by scanner controller 100. Backscattered scanning light rays 64 are also returned through window 60 to the rotating scanning mirror for reflection into a telescope 102, as will be further described. Light indications from telescope 102 are then further focused through optics 104 into the photomultiplier section 106. Photomultiplier section 106 is energized by DC power supply 108 and photomultiplier outputs are provided via conduit 110 to the system line termination circuits 112.

It should be noted that optics 104 consist of a plurality of beam splitting and focusing elements which may be disposed in diverse arrays with a respective plurality of photomultipliers 106, as will be further described. This is necessitated by the desirability of obtaining simultaneously or sequentially a plurality of continual oil fluorescence and scattering indications from backscattered scanning ray 64. While the basic indicator may be fluorescence amplitude at the water bottom 16, as well as at some designated spatial distance between bottom 16 and housing 50, it may also be desirable to include processing of the light data to derive differential light polarization data and/or differentially absorbed scattered energy (DASE). The use of combinations of such data indication, i.e. fluorescence, polarization and DASE will finally result in the provision of much more accurate data indication and pin pointing of oil seepage activity, as will be further described in detail.

The system within housing 50 includes conventional feedback and control circuits 114 for controlling laser 76 in proper mode of operation, and line interconnect 116 conducts the necessary control and monitor outputs. The control cable 118, as input from tow cable 24 and connector 56, includes AC power as input via bus 120 for routing to the cooling equipment 72 and several power supplies, and interconnect 122 provides communication for line termination circuits 112 as input from system monitor and multiplexer 90. Photomultiplier outputs on conduit 110 are then applied through line termination circuits 112 and conduit 124 to the tow vessel, and the output from interlock generator and sensors 126 is applied through line termination circuit 112 to conduit 126.

DC power to the system is provided by DC power system 98 via DC bus 128. Selected forms of conventional vehicle attitude sensors 130 are utilized to provide continual data output to the system monitor and multiplexer 90 which, in turn, provides output through termination circuits 112 and conduit 122 to the tow vessel for operator indication.

FIG. 5 illustrates in general block form the equipment maintained on board the tow vessel 10. The tow cable 24 is maintained in controlled storage on winch drum 132, and the electrical information from control conduit portion 118 is taken off by a slip ring assembly 134 and control cable 136 for interconnection to the shipboard equipment. AC power from generator 138 is applied on line 140 as well as through a control relay 142 to tow cable 24 when actuated by interlock signal from line termination circuits and demultiplexer 144.

Basic system timing is provided by a reference signal generator 146 which provides timing signals through termination circuits and demultiplexer 144 to the control cable 136. Reference signals from generator 146 are also applied to a lock-in amplifier 148 as well as the shipboard monitoring equipment. That is, data interchange between lock-in amplifier 148 and microcomputer 150 provide for processing of all derived data, and selected operator surveillance may be effected by use of an oscilloscope 152. Output from computer 150 is also applied to a CRT Monitor 154 under control of a keyboard 156, and computer output may be applied to a fiber optics plotter 158 for permanent recordation. A plurality of tape transports 160 are then available for recording of selected digital or analog data in accordance with operational requirements.

FIG. 6 illustrates a scanning system that may be utilized in the present invention to provide both fluorescence and polarization output from two selected focal points along the scanning path. That is, one lens system focuses at infinity to provide both fluorescence and polarization data from the entire water column extending from the submersible to the sea bottom; and another lens system focuses at a selected intermediate depth, e.g. 25 to 50 feet from sea bottom, to provide output of the fluorescence and polarization data. The fluorescence data is primarily indicative of oil presence while the polarization data gives a relative indication of the turbidity present in the water at the intermediate scanning focal point or along the entire extent that the beam propagates. One lens system can also be used to focus at the bottom to give fluorescence and polarization data at the sea floor.

Laser 76 functioning under power from laser power supply 78 provides optical output through an acousto-optic modulator 170, Harris Corp., Melbourne, Fla., through a beam splitter 84 and beam expander 172, Special Optics, Little Falls, N.J. The beam splitter 84 provides a component of laser output to a power meter 86 which provides control indication output via line 174 for return to shipboard and input to microcomputer system 176, Mod SBC 86/12, Intel Corporation, Santa Clara, Calif. Dash lines 178 indicate all system components which are located in shipboard.

The laser 76 in the preferred form is an Argon laser which emits laser output in eight different bands as follows:

|  | OUTPUT POWER-WATTS |
| --- | --- |
| 514.5 nanometers | 5.2 |
| 501.7 nanometers | 0.7 |
| 496.5 nanometers | 1.8 |
| 488.0 nanometers | 4.5 |
| 476.5 nanometers | 1.8 |
| 472.7 nanometers | 0.3 |
| 465.8 nanometers | 0.2 |
| 457.9 nanometers | 0.9 |

Of these emission wavelengths, those of highest power output are used for exciting oil to fluorescence for subsequent fluorescence detection in the range of 520–560 nanometers. Thus, utilization of the laser output at 514.5 nanometers will result in good output power thus increasing the range of the system adjacent the sea bottom. Laser 76 may be operated continuous wave, and it may be chopped by acousto-optic modulator 170; however, an electro-optic modulator or conventional optical chopper may be utilized as well. It should be understood that the Argon laser may also be operated using all output wavelengths simultaneously as this will result in a higher total oil fluorescence. Even though such lasing results in less power per individual component wavelength, the total power output is greater. This, together with the fact that oil absorbs shorter wavelengths better, may result in better conversion of light incident on oil to fluorescence emitted from that oil.

Beam expander 172 then provides adjustment for proper scanning beam size as the output beam 180 is 90° reflected from prism 92, Special Optics, Little Falls, N.J., and scanning member 94 to provide outgoing scanning light beam 62 traversing a swath line 182 at selected distance. The scanning member 94 is controlled by a velocity position control system 184, a commercially available control system from BEI Inc., Little Rock, Ark., and known as the ULTRA-LOC, a module which includes all of the scanner motor, encoders and scanner controller as shown in FIG. 4. Returned light beam 64 is then reflected from scanning member 94 into a folded telescope 102, an 8 inch Catadioptric Schmidt Cassegrain telescope, available from Celestron International, Torronce, Calif.

The light output 186 from telescope 102 proceeds to a fifty percent beam splitter 188, Mod 3-2203-2, Pomfret Research Optics, Inc., Stamford, Conn., for separation and to return light components 190 and 192 as directed onto respective lens systems 194 and 196. Prior to commencing operations, lens systems 194 and 196 are focused with the aid of viewing units 198 and 200. One lens system 196 is focused at infinity to provide an average signal value from a region extending from the bottom of the submersible to the sea bottom, while the other lens system 194 is focused at a selected intermediate distance between the submersible and the sea bottom. Each lens system can then provide indication of both fluorescence and polarization effects, as will be further described. Alternatively, one of the lens systems may be focussed directly on the sea floor.

Lens system 196, for example, may be focused at infinity to look at the entire water column that the laser beam traverses, and optical output through a pin hole aperture 202 and collimating lens 204 is passed through another beam splitter 206 to provide two output light components 208 and 210. The component 208 is light-filtered through a bandpass filter 211 passing light in the 520-560 nanometers waveband, i.e. the fluorescence zone of oil excited by the particular laser output, and this light is applied to a photomultiplier 212 which provides indicative output via a lead 214 to the lock-in amplifier 148. Thus, photomultiplier 212 output provides an indication in the form of a time analog voltage that represents the average amount of induced oil fluorescence that exits between the submersible and the sea bottom where the scanning beam traversed.

The other light component 210, from collimating lens 204 and beam splitter 206, is applied through yet another beam splitter 216 for passage through oppositely oriented light polarization filters 218 and 220 for detection at respective photomultipliers 222 and 224. Thus, as laser beam output is of a single polarization, detection of an indication of the ratio of polarization-shifted light relative to the outgoing polarization gives an indication of the amount of turbidity in the water (from the bottom of the submersible to the sea bottom in this case), i.e. turbidity or small particulate matter in the water gives rise to laser energy backscatter and de-polarization. The relative polarization outputs are provided from photomultipliers 222 and 224 via respective leads 226 and 228 to the lock-in amplifier 148 and, subsequently, into microcomputer system 176 for processing. The microcomputer system 176 then provides either a digital or a time analog output indication of sea bottom fluorescence and polarization ratio to a tape recorder 230 and other onboard operator equipment, such as television monitor 154 and fiber optics recorder 158.

The general technique of dual polarized laser backscatter for remote identification and measurement of water pollution is the subject of Texas A&M University Technical Report No. RSC-53, 1974, in the name of T. C. Sheives; and, Texas A&M University Interim Program Report No. 3, Coast Guard Contract No. RF3233, 1975, authored by A. J. Blanchard.

While lens system 196 serves to pinpoint oil seeps on the sea bottom, i.e. pipeline breaks, natural fault seeps, and the like, it is desirable to have lens system 194 focused at some selected height above the sea floor to provide indication of oil seepage plumes being carried along in the water current thereby to provide further indication of the direction and magnitude of the oil presence. Thus lens system 194 may be focused at a selected distance, e.g. midway between the submersible and the sea floor, to provide output of backscattered light from depth of field at that depth through a pin hole aperture 232 and collimator lens 234 to a beam splitter 236 which provides a first component of laser return through a bandpass light filter 238 (bandpass at 520-560 nanometers) to be seen by a photomultiplier 240. Photomultiplier 240 then provides the intermediate range fluorescence output, a time analog voltage present on lead 242 for input to the lock-in amplifier 148. The remaining portion of the return light from beam splitter 236 is then applied through a series beam splitter 244 to be passed through respective oppositely oriented polarization filters 246 and 248 to the respective photomultipliers 250 and 252. Indications of the oppositely polarized light components are then present on leads 254 and 256 for input to lock-in amplifier 148 and microcomputer system 176 for further processing and determination of ratio of polarization and water turbidity at the intermediate range.

The photomultipliers 212, 222, 224 and 240, 250, 252 are Mod 28-7326, OPTIMOD type available from Ealing Corporation, South Natick, Mass. The lock-in amplifier 148 is Mod 124A as acquired from Princeton Applied Research, Princeton, N.J.

Scanning synchronization of the velocity position control system 184 is controlled by microcomputer system 176 via leads 258 and 260 which are integral with the tow cable control system and lead up to shipboard and microcomputer system 176. In addition, commercially available forms of an inertial navigation system 262 (Honeywell MOD GEOSPIN) may be included on the submersible with communication to the shipboard and microcomputer system 176. Similarly, an acoustic position sensor suite 264 (Honeywell) utilized in conjunction with a satellite position system 266 (Mod 5010, Standford Telecom., Inc.) may be similarly disposed.

FIG. 7 illustrates an alternative form of oil indication which examines the differential absorption of scattered energy, i.e. the DASE system. The DASE system senses the effects of primarily Mie and Rayleigh scattering of the laser beam in water being examined. A scattering intensity indication is derived for fields of view at distance r as well as at distance $r + \Delta r$, and the differential values are further analyzed in view of known oil absorption coefficients. The system determines the concentration of a substance at an arbitrary point, distance r, by measuring the optical resonance absorption due to oil across an incremental path length, $\Delta r$. The absorption across $\Delta r$ is obtained from the relative attenuation of two collinear laser beams at closely spaced wavelengths $\lambda_1$ and $\lambda_2$, respectively, on and off of the resonance absorption of the molecule in question. Relative attenuation is determined from comparisons at the receiver of the Rayleigh and Mie elastic backscatter from the two laser beam wavelengths as they traverse the segment $\Delta r$.

For a pulsed laser source, appropriate temporal resolution at the receiver will permit determination of the range $r + \Delta r$, spatial resolution and distribution of the substance. For a continuous wave (CW) laser, focusing optics using a shallow depth of field receiver-telescope will yield the desired range, spatial resolution and distribution.

The system of FIG. 7 is described with operation in the synchronous detection mode, a form of CW detection using a modulated continuous wave light source. Synchronous detection is desirable from the standpoint that it increases the signal-to-noise ratio and tends to eliminate spurious light, sunlight, bioluminescence, etc. The source laser 76 is required to produce two or more wavelengths simultaneously (or sequentially in rapid sucession). This can also be achieved by selective filtering of a wide-band lamp, using appropriate intracavity optics with a nitrogen-laser-pumped dye laser or flash lamp-pumped dye laser, or any other simultaneous wavelength emitting source such as the Argon laser, as previously described. Light produced from laser 76 is modulated by acousto-optic modulator 170 under control of driver 171 at the system pulse rate from pulse generator 146. Output light beam from modulator 170 is partially deflected by beam splitter 84 to the power meter 86 and power indication is applied on lead 174 to the microcomputer system 176 where laser power fluctuations are compensated. Primarily, the light output passes through beam splitter 84 and beam expanding telescope 172 for output to the scanning assembly and undersea areas, as previously described.

Backscatter multi-wavelength light indications from the region examined are reflected back through the rotating mirror 94 and into the folded telescope 102 and along beam path 186 to a fifty percent beam splitter 270.

Fifty percent of the returned light from beam 186 is reflected into a lens system 272 which, with the aid of viewing unit 274, is focused at range r for projection of the light through a pin hole 276 and collimator 278 to fifty percent beam splitter 280. The pin hole 276 serves to reduce the field of view of receiver telescope 102 while maximizing the return signals backscattered from the source region within the depth of acceptance range r relative to those signals backscattered from surrounding source regions. The beam splitter 280 then directs one-half of the instant light through a pass band filter 282, the pass band matching one of the laser wavelengths $\lambda_1$ or $\lambda_2$, and photomultiplier 284 detects that backscattered laser energy emanating from the source region at range r.

Reference is made above to the depth of acceptance (DOA) and this refers to a region in space at range r from which light is collected by a receiver focussed at range r. DOA is defined as the distance plus and minus from the focal point of the receiver at which the value of collected light energy falls to 1/e of the value collected at the focal point.

The remaining fifty percent light beam from splitter 280 is passed through a pass band filter 286 whose pass band matches the second or remaining selected laser wavelength, either $\lambda_1$ or $\lambda_2$, and the returned energy is detected by photomultiplier 288. The respective $\lambda_1$ and $\lambda_2$ backscatter laser energy outputs at range r, as detected by photomultipliers 284 and 288, are then present on respective leads 290 and 292 for input to the lock-in amplifier 148.

The remaining fifty percent of light beam that passes through beam splitter 270 experiences the same type of optical processing as it is directed through lens system 294 having viewing unit 296; however, when system 294 is adjusted to focus at range $r + \Delta r$, the return is bounded by its respective depth of acceptance. Thus, light output through pin hole 298 and collimator 300 passes through beam splitter 302 with fifty percent of the light beam directed through a pass band filter 304, e.g. $\lambda_1$, with energy detection by photomultiplier 306 as output on lead 308. The remaining fifty percent of light from beam splitter 302 is applied through a pass band filter 310, e.g. $\lambda_2$, for detection by a photomultiplier 312 with signal output on leads 314 to lock-in amplifier 148. Thus, the photomultipliers 306 and 312 yield the received powers of the two lasing wavelengths $\lambda_1$ and $\lambda_2$ from the same region in space, viz. the depth of acceptance at range $r + \Delta r$. The four collected powers as output from photomultipliers 288, 284, 306 and 312 and input to lock-in amplifier 148 are then utilized along with known and manually set spatial resolution and absorption cross-sections, and this is all that is needed to determine the average concentration across the spatial resolution cell, $\Delta r$. These effective constants are known quantities for particular surveillance operation.

The photomultiplier outputs on leads 292, 290, 308 and 314 are applied to lock-in amplifier 148 which serves as a synchronous detector of the received backscattered signals. In practice, the backscatter signals are periodically received at the photomultiplier tubes at the same frequency at which the acousto-optic modulator 170 modulates the outgoing laser beams. These received signals at the modulator chop frequency are mixed with reference frequency equal to the chop frequency and as derived from the pulse generator 146 which simultaneously provides selected frequency input to the modulator driver 171 as well. This then guarantees that the modulated chop frequency is the same as the mixing frequency fed into the lock-in amplifier 148 as well as the chopped, backscattered laser beam return from the water or source region.

The phase between the periodically received laser backscattered signals and the chopped reference input to lock-in amplifier 148 is adjusted for maximum output from the lock-in amplifier stages. Outputs from lock-in amplifiers 148 are then applied to microcomputer system 176 where received data is collated with shift positions from the velocity position control system (see FIG. 6) as present on lead 260.

Referring again to FIG. 6, the acoustic position system 264 and satellite positioning system 266, are periodically transferred to the computer tape recorder 230, so location of the scanned region is known relative to the global coordinates. The inertial navigation system 262 may be used to compensate for any yaw, pitch and roll experienced by the submersible, and the output from inertial system 262 is also connected to the microcomputer system 176 to enable submersible movements to be directly collated with each scan of data.

The DASE system may also be readily utilized in combination with the basic fluorescence detection system, and FIG. 8 illustrates an optical system combining fluorescence and DASE probing while examining three different source regions between the submersible and water bottom. The system of FIG. 8 would utilize the same scanning and telescopic assemblies as previously discussed as output laser energy beam 180 reflects from prism 92 for scanning disposition, and received reflections from the scanning mirror 94 (FIG. 6, beam 64) are directed through telescope 102 to define returned energy beam 186. The energy beam 186 is directed through a fifty percent beam splitter 320 which divides the beam for direction as energy beam 322 to the DASE system 324, the remaining portion of the light beam 186 proceeding as beam 326 to the fluorescence data system 328.

In the fluorescence system 328, the primary input beam 326 is reflected from successive beam splitters 330 and 332 to provide light beam components into the lens systems 334, 336 and 338. The lens systems 334, 336 and 338 are each focused at a selected distance beneath the submersible, e.g. 25 feet, 50 feet, infinity, or at the sea floor; the infinity focus setting enabling fluorescence data to be collected from the entire water column that the laser beam travels, i.e. from the bottom of the submersible to the sea bottom.

Focused beam output from the lens systems 334-338 are then directed through respective pin holes 340, 342 and 344 and collimators 346, 348 and 350 for passage through respective bandpass filters 352, 354 and 356, each passing the oil fluorescence band in the area of 520-560 nanometers wavelength. Indications of the oil fluorescence are then sensed by respective photomultiplier 358, 360 and 362 with outputs being applied to lock-in amplifiers 364. Thus, the fluorescence system 328 of FIG. 8 functions in the same manner as the fluorescence sensors in FIG. 6 except that fluorescence data outputs are provided for three distinct focus areas defined by the depth of acceptance regions selected between the submersible and water bottom.

The remaining reflected primary beam 322 from beam splitter 320 is applied through a polarizing beam splitter 366 to provide output of a cross-polarized component 368 to a lens system 370. The remaining straight-through component 372 is then applied through a beam splitter 374 to be directed through lens systems 376 and 378. The lens systems 376, 378 and 370 are again focused for differing depth of acceptance such that focus of the lens systems may be set, for example, 25 feet, 50 feet and water column. As will be described, the photomultiplier combinations will look at backscattered laser energy at essentially the same frequency as the outgoing laser beams, and in this case two distinct laser beam wavelengths are utilized simultaneously or alternately. Thus, the cross-polarized light component from lens system 370 is directed through a pin hole 380, collimator 382 and beam splitter 384 to be directed through bandpass filters 386 and 388, $\lambda_1$ and $\lambda_2$ respectively.

The laser backscatter return at the two lasing wavelengths is then detected by the respective photomultipliers 390 and 392 with output provided to the lock-in amplifiers 364. The dual wavelength, cross-polarization output enables input of a reference de-polarization level to the microcomputer system 176 (see FIG. 7). In clear waters, free from turbidity, any cross-polarization signals that are detected by photomultipliers 390 and 392 represent laser backscattered signals from the ocean bottom. The outgoing polarized laser beam is de-polarized when it hits the sea bottom. Photomultipliers 390 and 392 detect the de-polarized (or cross-polarized) signal backscattered from the sea bottom.

Lens systems 376 and 378 are then directed to the focus of the DASE data as they define a cell region of known dimension or $\Delta r$ for examination of both wavelengths $\lambda_1$ and $\lambda_2$ to determine the presence of oil above the sea bottom. Lens system 376 directs backscatter laser return through a pin hole 394 and collimator 396 through beam splitter 398 which directs light energy through the $\lambda_1$ and $\lambda_2$ bandpass filters 400 and 402. The light energy at wavelengths $\lambda_1$ and $\lambda_2$ are then detected by photomultipliers 404 and 406 with outputs to the lock-in amplifiers 364. In like manner, the lens system 378, functioning with pin hole 408, collimator 410 and beam splitter 412, directs light through the $\lambda_1$ and $\lambda_2$ bandpass filters 414 and 416 for detection by the respective photomultipliers 418 and 420. All of the photomultiplier outputs are applied through an amplifier section of the lock-in amplifiers 364 with synchronous outputs for conduction to the microcomputer system.

It should be understood that still other detection schemes may be utilized in carrying out the basic method of the invention. It is contemplated that higher power pulsed laser sources or CW laser sources may be utilized in shallow water investigation by scanning energy directly from the surface vessel or other hardconnected appendage therefrom. One form of surveillance enabling inclusion of nearly all electronic equipment onboard the survey vessel would be in utilizing fiber optics cable transmission of source energy down to the underwater locale with return of reflected or fluorescent light indications. Another alternative method of oil detection in the subsurface is that where the detection system looks for Raman scattering. A system similar to the DASE system of FIG. 7 may be utilized for Raman scattering detection simply by changing the band widths of the interference filters to include wavelengths of the Raman bands induced in oil or whatever the underwater survey subject.

While the foregoing description proceeds primarily utilizing a CW energy source, it is well within the contemplation of the inventors that either of the fluorescence detection or DASE process may be carried out with a pulsed light system as utilized with suitable scanning device, telescope, fiber optics or the like. In addition, the coaxial laser-mirror configuration as depicted herein may well be changed to an off-axis source-receiver device, and this mode of operation may help in reducing background levels and obtaining fluorescence data directly from the sea bottom.

The foregoing discloses a method and complete system apparatus for carrying out underwater surveillance of selected water bottom areas in order to determine the presence of hydrocarbons. In examining the water bottom, the method takes into account the possible presence of organic life and turbidity which could contribute to the hydrocarbon presence readout; however, possible spurious readout values are differentiated so that subsequent data processing enables a true readout of the hydrocarbon presence. The apparatus is directed to a capability for scanning both the water bottom and a selected column intermediate the water bottom and submersible as well as above and to the side of the submersible thereby to enable tracking of hydrocarbon currents as well as location of specific seep points on the bottom. Thus, the present method and apparatus may be utilized as a tool not only for pollution monitoring and pipeline inspection, but also in conjunction with seismic surveying vessels working the similar survey traverses.

Changes may be made in combination and arrangement of elements as heretofore set forth in the specification and shown in the drawings; it being understood that changes may be made in the embodiments disclosed without departing from the spirit and scope of the invention as defined in the following claims.

The embodiments of the invention in which an exclusive property or privilege is claimed are defined as follows:

1. A method for detecting presence of hydrocarbons within a body of water proximate the water bottom comprising:
   moving an instrument platform through said body of water at a pre-selected distance above the water bottom;
   generating light energy and directing said light energy from said instrument platform toward a selected area within the body of water as a repetitive scanning beam on said water bottom transverse to the line of movement of said instrument platform;
   detecting selected fluorescence excitation resulting from said light energy; and
   providing a data readout of said fluorescence excitations as an indication of hydrocarbon presence.

2. A method as set forth in claim 1 wherein said step of detecting comprises:
   detecting fluorescence excitation to said water bottom; and
   detecting fluorescence excitation in the water intermediate said water bottom and the instrument platform.

3. A method as set forth in claim 1 wherein said step of generating light energy, comprises:
   energizing a laser having a selected wavelength output that excites water-suspended hydrocarbons to fluorescence.

4. A method as set forth in claim 3 wherein said step of detecting comprises:
   detecting light energy within a selected band of wavelengths from approximately 520 nanometers to 560 nanometers.

5. A method as set forth in claim 1 which further comprises:
   detecting backscattered light energy to derive an indication of water turbidity in the area of fluorescence excitation.

6. A method as set forth in claim 5 wherein the step of detecting backscattered light energy comprises:
   detecting backscattered light energy at said water bottom; and
   detecting backscattered light energy in the water intermediate said water bottom and the instrument platform.

7. A method as set forth in claim 5 wherein said step of detecting backscattered light energy comprises:
   sensing oppositely polarized components of said backscattered light energy to establish a ratio of polarization indicative of the degree of water turbidity.

8. A method as set forth in claim 6 wherein said steps of detecting backscattered light energy each comprises:
   sensing oppositely polarized components of said backscattered light energy to establish a ratio of polarization indicative of the degree of water turbidity.

9. A method for detecting presence of hydrocarbons within a body of water using a submersible instrument platform, comprising:
   generating a beam of light energy of selected wavelength from within said platform;
   repetitively scanning said beam through a transverse path beneath said platform;
   telescopically receiving within the platform the light return caused by said scanning beam to provide an output light beam;
   viewing return light from said output light beam at a first depth of field to provide a first focused light output;
   simultaneously viewing return light from said output light beam at a second depth of field to provide a second focused light output; and
   providing electrical signal outputs of said first and second focused light outputs as an indication of hydrocarbon presence.

10. A method as set forth in claim 9 wherein said steps of viewing and simultaneously viewing comprise:
    focusing said output light beam at infinity to provide scanning coverage of the water to the bottom; and
    focusing said output light beam on at least one selected point intermediate said water bottom and said platform.

11. A method as set forth in claim 9 which is further characterized to include steps of:
    examining said first focused light output within a selected wavelength band to provide as an output a hydrocarbon fluorescence indication; and
    examining said second focused light output within a second selected wavelength band to provide an indication of backscattering of the generated beam of light energy.

12. A method as set forth in claim 10 wherein said step of providing electrical signal outputs further comprises:
    examining said first focused light output within a selected wavelength band to provide an output hydrocarbon fluorescence indication;
    examining said second focused light output within said selected wavelength band to provide a second output hydrocarbon fluorescence indication;
    examining said first focused light output within a second selected wavelength band to provide an output indication of backscattering of the generated beam of light energy; and
    examining said second focused light output within said second selected wavelength band to provide a second output indication of backscattering of the generated beam of light energy.

13. A method as set forth in claim 12 wherein said steps of examining said first and second focussed light outputs within said second selected wavelength band to provide an output indication of backscattering of the generated beam of light energy, each comprise:
    separating the respective focussed light outputs to provide two oppositely oriented polarized light outputs; and
    sensing the oppositely polarized light output components to derive an output ratio of one component relative to the other which is an indication of turbidity of water at the particular depth of acceptance.

14. A system for underwater detection of hydrocarbon substance, comprising:
    a submersible platform;
    means generating a light beam on board said platform;

means for scanning and receiving reflection of said light beam through a transverse arcuate sector beneath said platform;

telescope means within said platform receiving reflection of said light beam to provide an output light beam;

lens means receiving said output light beam and being focussed to project light from selected depths of acceptance; and photoelectric means receiving said projected light and generating an output electrical signal indicative of hydrocarbon presence.

15. A system as set forth in claim 14 wherein said lens means comprises:

first lens means projecting first light output from a selected depth of acceptance; and second lens means projecting second light output from a selected different depth of acceptance.

16. A system as set forth in claim 15 wherein said photoelectric means comprises:

means detecting fluorescence within a selected wavelength band from said first and second light outputs.

17. A system as set forth in claim 15 wherein said photoelectric means comprises:

means detecting backscattered light beam energy of selected wavelength from said first and second light outputs.

18. A system as set forth in claim 14 wherein said photoelectric means comprises:

means detecting fluorescence within a selected wavelength band from said projected light.

19. A system as set forth in claim 14 wherein said photoelectric means comprises:

means detecting orthogonal polarization components of backscattered light beam energy from said projected light.

20. A system as set forth in claim 18 wherein said photoelectric means further comprises:

means detecting orthogonal polarization components of backscattered light beam energy from said projected light.

21. A system as set forth in claim 16 wherein said photoelectric means further comprises:

means detecting orthogonal polarization components of backscattered light beam energy from said first and second light outputs.

22. A system as set forth in claim 14 wherein said means generating a light beam comprises:

a laser having a selected wavelength output that excites water-suspended hydrocarbons to fluorescence.

23. A system as set forth in claim 22 wherein said photoelectric means includes:

means for detecting light energy within a selected band of wavelengths from approximately 520 nanometers to 560 nanometers.

* * * * *